United States Patent [19]
Diaz et al.

[11] Patent Number: 5,942,531
[45] Date of Patent: Aug. 24, 1999

[54] PHENOLIC/NAPHTHOLIC RETINOIDS FOR PROMOTING SKIN/EXOSKELETON PIGMENTATION

[75] Inventors: Philippe Diaz, Nice; Bruno Charpentier, Biot; Braham Shroot, Antibes, all of France

[73] Assignee: Centre International de Recherches Dermatologiques, Valbonne, France

[21] Appl. No.: 09/021,396

[22] Filed: Feb. 10, 1998

[30] Foreign Application Priority Data

Feb. 10, 1997 [FR] France .................................. 97 01500

[51] Int. Cl.$^6$ .................................................. A61K 31/415
[52] U.S. Cl. ......................... 514/394; 514/569; 514/568; 514/544; 514/456; 514/469; 514/443
[58] Field of Search .................... 514/568, 569, 514/544, 556, 469, 443, 394

[56] References Cited

FOREIGN PATENT DOCUMENTS

| 92-106283 | 4/1992 | European Pat. Off. . |
|---|---|---|
| WO 97-US11564 | 7/1997 | WIPO . |

OTHER PUBLICATIONS

Albert Muller International—Cosmet. News, 19(106), 50–54, Italy (Abstract), 1996.

Primary Examiner—James H. Reamer
Attorney, Agent, or Firm—Burns, Doane, Swecker & Mathis, L.L.P.

[57] ABSTRACT

Pigmentation of the skin, hair and/or nails of individuals is promoted by administering thereto, advantageously topically and advantageously in combination with enzymes exhibiting tyrosinase activity, effective pigmentation-promoting amounts of at least one retinoid compound which comprises a phenolic or naphtholic functional group.

23 Claims, No Drawings

PHENOLIC/NAPHTHOLIC RETINOIDS FOR PROMOTING SKIN/EXOSKELETON PIGMENTATION

CROSS-REFERENCE TO PRIORITY APPLICATION

This application claims priority under 35 U.S.C. §119 of FR-01500, filed Feb. 10, 1997, hereby expressly incorporated by reference.

BACKGROUND OF THE INVENTION

1. Technical Field of the Invention

The present invention relates to novel cosmetic/pharmaceutical compositions for promoting pigmentation of the skin and/or the exoskeleton thereof, comprising at least one retinoid bearing a phenol or naphthol functional group.

This invention also relates to a cosmetic regime or regimen for pigmenting the skin and/or exoskeleton thereof, comprising administering to an individual in need of such treatment at least one retinoid bearing a phenol or naphthol function.

2. Description of the Prior Art

The coloration of human skin and exoskeleton thereof (head hair, nails, other hair, etc.) depends on various factors and especially on the seasons of the year, race, sex and age. It is determined, principally, by the concentration of melanin produced by the melanocytes. The melanocytes are specialized cells which synthesize melanin by means of specific organelles, the melanosomes.

It is known to this art that in most populations brown skin color or the maintenance of a constant head of hair color are important aspirations.

Moreover, pigmentation diseases exist such as, for example, vitiligo which is an auto-immune disease characterized by the appearance of white patches on the skin, associated with a pigmentation defect.

Serious need thus exists for a product which facilitates and/or improves the pigmentation of the skin and/or its exoskeleton, more particularly the hair and the nails.

To date, various solutions have been proposed to the art of artificial coloration, by supplying exogenous dyes that are intended to color the skin and/or the hair to an extent as close as possible to its natural color, or in the field of natural coloration via stimulation of the natural pigmentation pathways.

Excellent results are, admittedly, obtained via the solutions heretofore proposed, but it nevertheless remains that the stimulation of pigmentation of the skin or exoskeleton thereof via the natural route (melanogenesis) remains the ideal pigmentation route.

In this regard, administration of compositions containing a phosphodiesterase inhibitor, prostaglandins, DNA fragments, tyrosine derivatives or, alternatively, plant extracts have been proposed; see WO-A-95/17161, WO-95/11003, WO-A-95/01773, WO-A-94/04674, WO-A-94/04122, EP-A-585,018, WO-A-93/10804, WO-A-92/20322 and WO-A-91/07945. Often, the proposed compounds are complex mixtures which exhibit no specificity.

Hence, identification of active species eliciting a beneficial effect on the pigmentation of the skin or exoskeleton remains a principal desideratum in this art.

SUMMARY OF THE INVENTION

Accordingly, a major object of the present invention is the provision of novel compounds for promoting pigmentation of the skin and/or exoskeleton of individuals in need of such treatment.

Briefly, it has now unexpectedly and surprisingly been determined that certain retinoids induce melanogenesis and thus promote pigmentation of the skin or its exoskeleton. This is all the more surprising since other retinoids have been described as depigmenting agents. Thus, all-trans-retinoic acid has been described as an agent for lightening hyperpigmented marks on the skin (J. S. Weiss et al., "Topical tretinoin improves photodamaged skin," *J. Am. Med. Assoc.*, 259, 527–532 (1988)). Furthermore, the combination of vitamin A derivatives and antioxidants such as quinones or flavonoid derivatives is known to reduce the level of melanin both in hyperpigmented skin and in normal skin (U.S. Pat. No. 3,856,934, EP-421,110, JP-60/48934, JP-63/301,810).

Thus, the present invention features cosmetic/pharmaceutical compositions comprising, as the active principle thereof, an effective amount of at least one retinoid bearing a phenol or naphthol function, for promoting pigmentation of the skin and/or exoskeleton thereof.

This invention also features a cosmetic treatment, regime or regimen for pigmenting the skin and/or exoskeleton thereof, comprising administering to an individual in need of such treatment, advantageously topically, at least one retinoid bearing a phenol or naphthol function, formulated into suitable carrier, vehicle or diluent therefor.

The invention also features cosmetic/pharmaceutical compositions comprising, in a physiologically acceptable support (vehicle, diluent or carrier), at least one retinoid bearing a phenol or naphthol function and at least one substrate of at least one enzyme exhibiting tyrosinase activity.

DETAILED DESCRIPTION OF BEST MODE AND SPECIFIC/PREFERRED EMBODIMENTS OF THE INVENTION

More particularly according to the present invention, among the exoskeletal embodiments thereof, the hair or the nails are most representative.

By the expression "retinoid bearing a phenol or naphthol function" are intended compounds which have both:

(1) retinoid-type biological activity, i.e., acting on cell proliferation and differentiation, as defined in L. J. Gudas et al., pp. 443–520, Chapter 11, "Cellular Biology and Biochemistry of the Retinoids", in *Retinoids, Biology, Chemistry and Medicine,* (1994), and in Sporn, M. D. Roberts, A. B., Goodman, D. S., published by Raven Press; Pawson et al., "Retinoids at the threshold: their biological significance and therapeutic potential," *J. Med. Chem.*, 25, 1269–1277 (1982), and (2) a phenol or naphthol functional group, in free or protected form.

Retinoids containing a phenol function are the preferred.

Among the protecting groups for the phenol or naphthol function, an ether or ester group is preferred.

These protecting groups are described, in particular, in the text, "Protective Groups in Organic Synthesis", by Theodora W. Greene and Peter G. Wuts, Ed. John Wiley and sons, 1991.

Exemplary retinoids bearing a phenol or naphthol function, particularly representative are the following compounds:

6-[3-(1-adamantyl)-4-methoxyphenyl]-2-naphthoic acid;

methyl 6-[3-(1-adamantyl)-hydroxyphenyl]-2-naphthoate;

6-[3-(1-adamantyl)-4-hydroxyphenyl]-2-naphthoic acid;

6-[3-(1-adamantyl)-4-acetoxyphenyl]-2-naphthoic acid;

[3-[3-(1-adamantyl)-4-methoxyphenyl]-2H-1-benzopyran]-7-carboxylic acid;

[3-[3-(1-adamantyl)-4-hydroxyphenyl]-2H-1-benzopyran]-7-carboxylic acid;

[3-[3-(1-adamantyl)-4-acetoxyphenyl]-2H-1-benzopyran]-7-carboxylic acid;

[2-[3-(1-adamantyl)-4-hydroxyphenyl]benzimidazole]-5-carboxylic acid;

[2-[3-(1-adamantyl)-4-hydroxyphenyl]benzothiophene-6-carboxylic acid;

[2-[3-(1-adamantyl)-4-hydroxyphenyl]benzofuran-6-carboxylic acid;

4-[(E)-2-[3-(1-adamantyl)-4-hydroxyphenyl]propenyl]-benzoic acid;

4-[2-[3-(1-adamantyl)-4-hydroxyphenyl]ethynyl]benzoic acid;

3-[(3,5-di-tert-butyl-4-hydroxyphenyl)-2H-1-benzopyran]-7-carboxylic acid;

methyl 3-[(3,5-di-tert-butyl-4-hydroxyphenyl)-2H-1-benzopyran]-7-carboxylate;

6-[3-tert-butyl-4-hydroxyphenyl]naphthoic acid;

4-[(E)-2-[3,5-di-tert-butyl-4-hydroxyphenyl]ethenyl] benzoic acid;

4-[(E)-2-[3,5-di-tert-butyl-4-hydroxyphenyl]propenyl] benzoic acid;

4-[3-(3,5-di-tert-butyl-4-hydroxyphenyl)-1-propynyl] benzoic acid;

(all-E)-9-(3-(1-adamantyl)-4-hydroxyphenyl)-3,7-dimethyl-2,4,6-nonatrienoic acid;

(all-E)-9-(4-hydroxy-2,3,6-trimethylphenyl)-3,7-dimethyl-2,4,6,8-nonatetraenoic acid;

ethyl (all-E)-9-(4-methoxy-2,3,6-trimethylphenyl)-3,7-dimethyl-2,4,6,8-nonatetraenoate;

4-[6-hydroxy-7-(1-adamantyl)-2-naphthyl]benzoic acid;

4-[(E)-2-[3-tert-butyl-4-hydroxyphenyl)propenyl] benzoic acid;

The above compounds have the respective structural formulae (1) to (23) below:

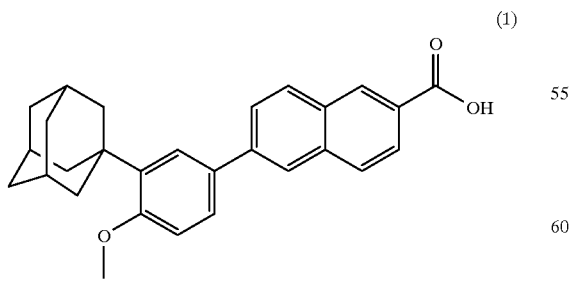

(1)

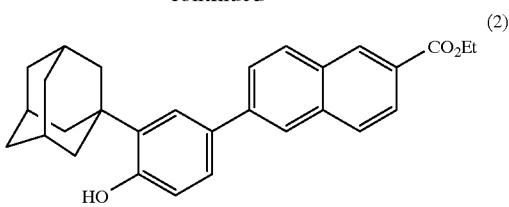

(2)

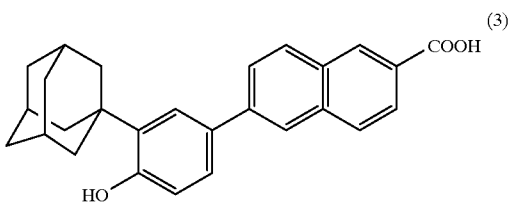

(3)

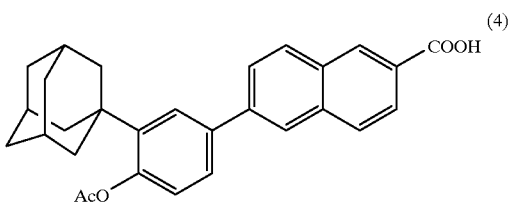

(4)

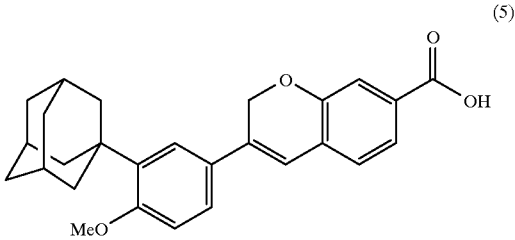

(5)

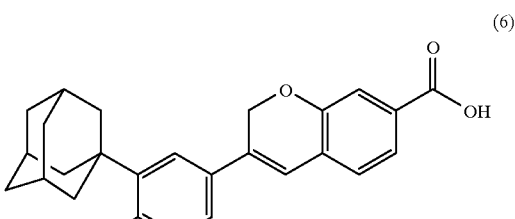

(6)

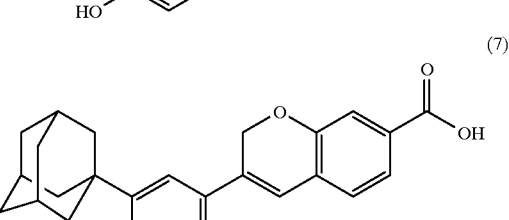

(7)

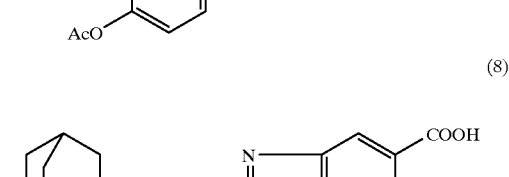

(8)

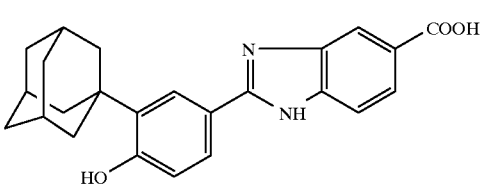

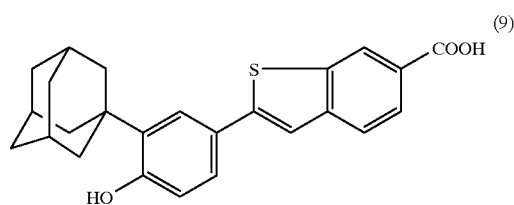
(9)
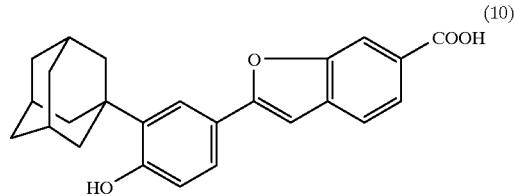
(10)
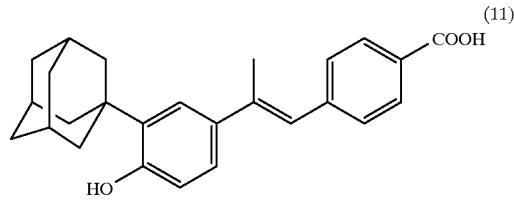
(11)
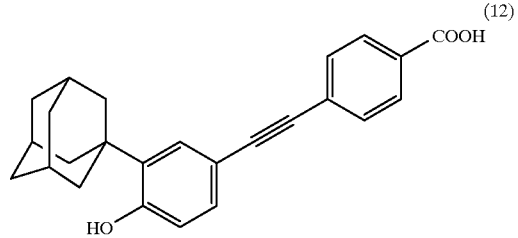
(12)
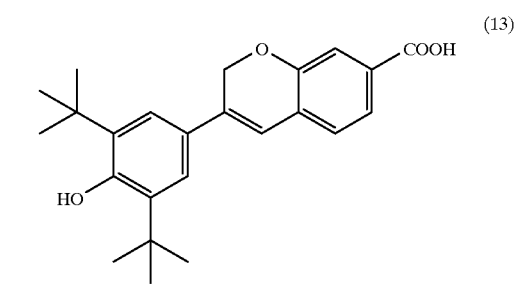
(13)
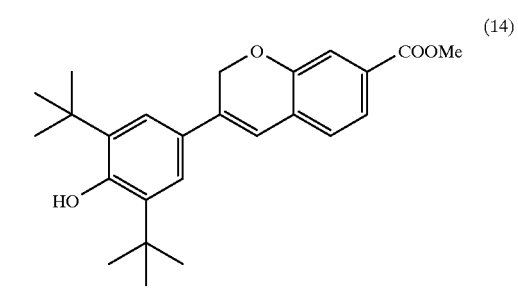
(14)
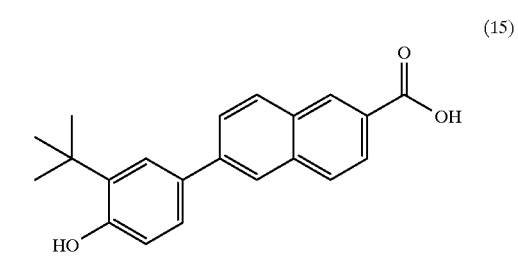
(15)
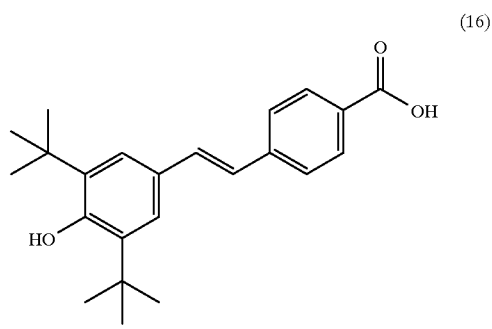
(16)
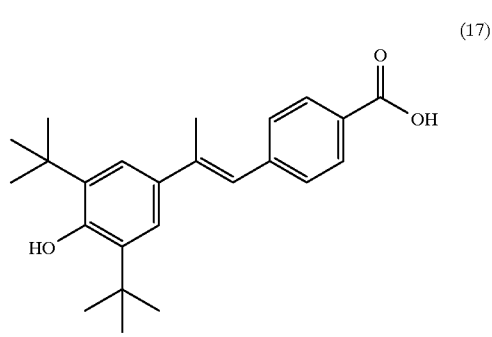
(17)
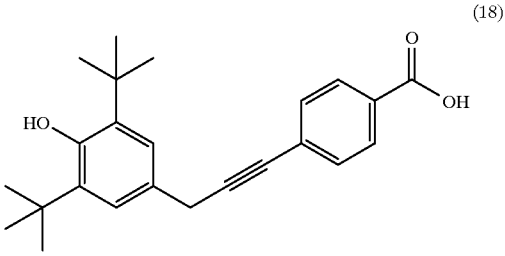
(18)
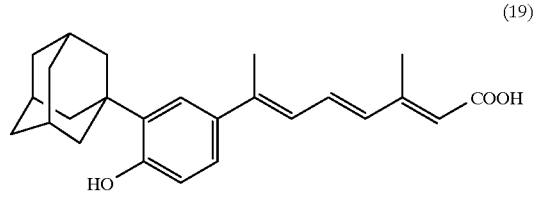
(19)
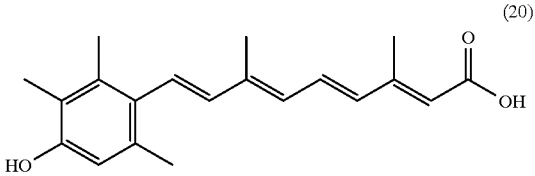
(20)
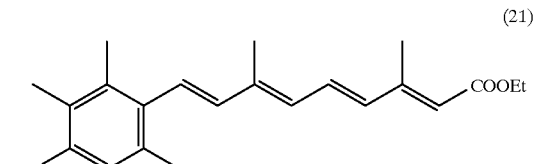
(21)
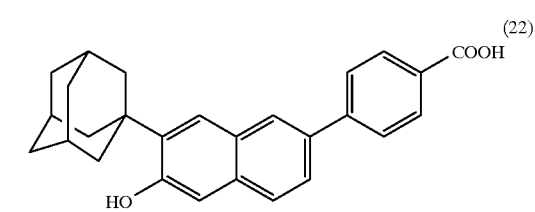
(22)

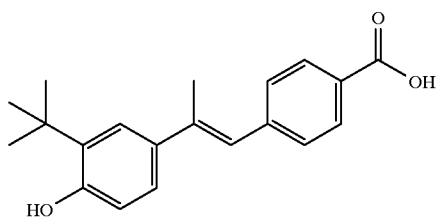

(23)

Among these, preferred are the following retinoids bearing a phenol or naphthol function:

6-[3-(1-adamantyl)-4-hydroxyphenyl]-2-naphthoic acid;
4-[(E)-2-[3-(1-adamantyl)-4-hydroxyphenyl]propenyl]-benzoic acid;
3-[(3,5-di-tert-butyl-4-hydroxyphenyl)-2H-1-benzopyranl-7-carboxylic acid;
4-[(E)-2-[3,5-di-tert-butyl-4-hydroxyphenyl]propenyl] benzoic acid;
4-[3-(3,5-di-tert-butyl-4-hydroxyphenyl)-1-propynyl] benzoic acid.

The retinoids according to the invention are useful for medical or convenience (cosmetic) purposes. They are useful, in particular, for the treatment of pigmentation afflictions such as vitiligo, albinism, post-inflammatory hypopigmentations, for the treatment of hypopigmentations or depigmentations after skin grafts, for the treatment of hypopigmentations or depigmentations due to overexposure to ultraviolet rays, for treating post-cicatrization hypopigmentations or depigmentations or for treating hypopigmentations or depigmentations due to aging or lentigo. They are also useful to recolor the hair, more particularly grey hair, or to treat nail pigmentation afflictions/conditions.

This invention also features cosmetic or pharmaceutical composition comprising, in a physiologically acceptable support, at least one retinoid bearing a phenol or naphthol function and at least one substrate of at least one enzyme exhibiting tyrosinase activity.

Among such substrates, representative are, for example, tyrosine or derivatives thereof, 3,4-dihydroxyphenyl-α-alanine (DOPA) or 5,6-dihydroxyindole.

The retinoid and the substrate can be combined in a single composition. However, specific other embodiments are also envisaged, in particular administering the retinoid and the substrate simultaneously, separately or spread out over time.

Thus, the present invention features compositions comprising at least one retinoid containing a phenol or naphthol function and at least one substrate of at least one enzyme exhibiting tyrosinase activity, as a combination product for simultaneous or separate use or for use spread out over time in order to promote pigmentation of the skin and/or the hair.

In one specific embodiment, the retinoid and the substrate can be packaged separately in the form of a kit whose components will be mixed together at the time of use.

Too, this invention features a kit comprising at least one retinoid containing a phenol or naphthol function and at least one substrate of at least one enzyme having tyrosinase activity, for simultaneous or separate use or for use divided over time to promote pigmentation of the skin and/or exoskeleton thereof.

The compositions comprising the retinoid according to the invention can be ingested, injected or topically applied to the skin (to any area of body skin) or its exoskeleton, more particularly the hair and the nails. Depending on the mode of administration, the compositions according to the invention can be formulated in any pharmaceutical form.

The effective or sufficient amount of retinoids administered or contained in the subject compositions obviously corresponds to the amount required to promote the expected pigmentation, such amount depending in particular on the pigmenting quality of the retinoid selected and on the composition in which it is formulated, as well as the frequency with which the composition comprising the retinoid is administered.

Via the enteral route, the medicinal products can be in the form of tablets, gelatin capsules, sugar-coated tablets, syrups, suspensions, solutions, powders, granules, emulsions, microspheres or nanospheres, or lipid or polymer vesicles permitting controlled release.

In order to provide an order of magnitude, the ingested or injected retinoids according to the invention are generally administered at a daily dose of 0.01 mg/kg to 100 mg/kg of bodyweight, approximately, in 1 to 3 dosages.

For topical application to the skin, the subject compositions can be in the form, in particular, of an aqueous or oily solution, or of a dispersion of the lotion or serum type, emulsions of liquid or semi-liquid consistency of the milk type, obtained by dispersing a fatty phase in an aqueous phase (O/W) or conversely (W/O), or suspensions or emulsions of soft consistency of the aqueous or anhydrous cream or gel type, or alternatively microcapsules or microparticles, or vesicle dispersions of ionic and/or nonionic type. These compositions are formulated via the conventional techniques.

They can also be administered to the hair in the form of aqueous, alcoholic or aqueous-alcoholic solutions, or in the form of creams, gels, emulsions or mousses, or alternatively in the form of aerosol compositions also comprising a propellant under pressure.

The compositions according to the invention can also comprise a haircare composition, and in particular a shampoo, a hairsetting lotion, a treating lotion, a styling cream or gel, a dye composition (in particular an oxidation dye composition) optionally in the form of dyeing shampoos, restructuring lotions for the hair, a permanent-waving composition (in particular a composition for the first stage of a permanent-waving operation), a lotion or gel for preventing hair loss, an antiparasitic shampoo, etc.

For administdration by injection, the compositions are advantageously in the form of an aqueous or oily lotion, or in the form of a serum, and, for ingestion, they are advantageously formulated as capsules, granules, syrups or tablets.

The amounts of the various constituents of the compositions according to the invention are those conventionally employed in this art.

The compositions may also comprise solid preparations which constitute cleansing soaps or bars.

The subject compositions can also be packaged in the form of an aerosol composition also comprising a propellant under pressure.

When the subject compositions comprise an emulsion, the proportion of the fatty phase therein can range from 5% to 80% by weight, and preferably from 5% to 50% by weight, relative to the total weight of the composition. The oils, the waxes, the emulsifiers and the co-emulsifiers formulated into the composition in emulsion form are selected from among those that are conventional in the cosmetic field. The emulsifier and the co-emulsifier are typically present in the composition in a proportion ranging from 0.3% to 30% by weight, and preferably from 0.5% to 20% by weight, relative to the total weight of the composition. In addition, such emulsifiers can also contain lipid vesicles.

When the compositions of the invention are formulated as oily gels or solutions, the fatty phase thereof can constitute more than 90% of the total weight of the composition.

These compositions for topical application contain at least one retinoid bearing a phenol or naphthol function according to the invention at a concentration preferably ranging from 0.001% to 5% relative to the total weight of the composition.

The concentration of retinoid bearing a phenol or naphthol function according to the invention in the topically applicable cosmetic compositions preferably ranges from 0.001% to 3% by weight.

In known manner, the subject cosmetic compositions can also contain adjuvants and additives that are conventional in the cosmetic field, such as hydrophilic or lipophilic gelling agents, hydrophilic or lipophilic additives, preservatives, antioxidants, solvents, fragrances, fillers, screening agents, odor absorbers, dyestuffs and colorants. The amounts of these various adjuvants and additives are those that are conventional in the cosmetic field, and, for example, range from 0.01% to 10% of the total weight of the composition. Depending on their nature, these adjuvants and additives can be introduced into the fatty phase, into the aqueous phase and/or into the lipid spherules.

Exemplary oils or waxes which are suitable according to this invention include mineral oils (liquid petroleum jelly), plant oils (liquid fraction of karite butter, sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) can be added to these oils.

Exemplary emulsifiers include, for example, glyceryl stearate, polysorbate 60 and the mixture PEG-6/PEG-32/glycol stearate marketed under the trademark Tefose® 63 by Gattefosse.

Exemplary solvents include the lower alcohols, in particular ethanol and isopropanol, and propylene glycol.

And exemplary hydrophilic gelling agents according to the present invention include the carboxyvinyl polymers (carbomer), acrylic copolymers such as acrylate/alkylacrylate copolymers, polyacrylamides, polysaccharides such as hydroxypropyl-cellulose, natural gums and clays, and exemplary lipophilic gelling agents include the modified clays such as bentones, metal salts of fatty acids such as aluminum stearates and hydrophobic silica, ethylcellulose and polyethylene.

The subject compositions can also contain other hydrophilic active agents such as proteins or protein hydrolysates, amino acids, polyols, urea, allantoin, sugars and sugar derivatives, water-soluble vitamins, plant extracts and hydroxy acids, etc.

Retinol (vitamin A) and derivatives thereof, tocopherol (vitamin E) and derivatives thereof, essential fatty acids, ceramides, essential oils, and salicylic acid and derivatives thereof are representative lipophilic active agents.

According to the invention, the subject compositions can combine at least one retinoid containing a phenol or naphthol function with at least one other active agent. Exemplary of such "other" active agents are:

(a) agents which improve activity in respect of hair regrowth and/or retarding hair loss, and which are already known to the art for such activity, such as, for example, nicotinic acid esters including, in particular, tocopheryl nicotinate, benzyl nicotinate and $C_1$–$C_6$ alkyl nicotinates such as methyl or hexyl nicotinate, and active agents which promote hair regrowth, such as those described in EP-0,648,488, assigned to the assignee hereof;

(b) antibacterial agents such as clindamycin phosphate, erythromycin or antibiotics of the tetracycline class;

(c) antiparasitic agents, in particular metronidazole, crotamiton or pyrethroids;

(d) antifungal agents, in particular compounds belonging to the imidazole class, such as econazole, ketoconazole or miconazole or salts thereof, polyene compounds such as amphotericin B, compounds of the allylamine family such as terbinafine, or, alternatively, octopirox;

(e) antiviral agents such as acyclovir;

(f) steroidal anti-inflammatory agents such as hydrocortisone, betamethasone valerate or clobetasol propionate, or non-steroidal anti-inflammatory agents such as, for example, ibuprofen and salts thereof, diclofenac and salts thereof, acetylsalicylic acid, acetaminophen or glycyrhizic acid;

(g) anaesthetic agents such as lidocaine hydrochloride and derivatives thereof;

(h) anti-pruriginous agents such as thenaldine, trimeprazine or cyproheptadine, (i) keratolytic agents such as α- and β-hydroxycarboxylic acids or β-ketocarboxylic acids, salts, amides or esters thereof and more particularly the hydroxy acids such as glycolic acid, lactic acid, salicylic acid, citric acid and fruit acids in general, and 5-n-octanoylsalicylic acid;

(j) anti-free-radical agents such as α-tocopherol or esters thereof, superoxide dismutases, certain metal-chelating agents or ascorbic acid and esters thereof;

(k) anti-seborrhoeic agents such as progesterone;

(l) antidandruff agents such as octopirox or zinc pyrithione;

(m) antiacne agents such as benzoyl peroxide.

Other such active agents include, for example, Diazoxide, Spiroxazone, phospholipids such as lecithin, linoleic acid, linolenic acid, salicylic acid and derivatives thereof described in FR-2,581,542, such as salicylic acid derivatives bearing an alkanoyl group having from 2 to 12 carbon atoms in position 5 of the benzene ring, hydroxycarboxylic acids or ketocarboxylic acids and esters thereof, lactones and the corresponding salts thereof, anthralin, carotenoids, eicosatetraenoic and eicosatrienoic acids or esters and amides thereof, vitamin D and derivatives thereof, and extracts of plant or bacterial origin.

Thus, in one specific embodiment, the compositions according to the invention also comprise at least one active agent selected from among the antibacterial agents, antiparasitic agents, antifungal agents, antiviral agents, anti-inflammatory agents, anti-pruriginous agents, anaesthetics, keratolytic agents, anti-free-radical agents, anti-seborrhoeic agents, antidandruff agents, antiacne agents and/or agents which reduce skin differentiation and/or proliferation and/or pigmentation, and extracts of plant or bacterial origin.

The subject compositions advantageously comprise at least one retinoid compound containing a phenol or naphthol functional group which is in liposomal form, as described in WO-94/22468, filed Oct. 13, 1994, assigned to Anti Cancer Inc. Thus, such compounds encapsulated in liposomes can be selectively administered/delivered to the hair follicles.

One skilled in this art will of course take precautions not to incorporate compounds into the compositions of the present invention such that these compounds counteract the desired technical effect provided thereby.

The pharmaceutical compositions according to the invention can be administered parenterally, enterally or topically. Preferably, the pharmaceutical compositions are administered topically.

In order to further illustrate the present invention and the advantages thereof, the following specific examples are given, it being understood that same are intended only as illustrative and in nowise limitative.

EXAMPLE 1

Pigmenting activity of retinoids containing a phenol naphthol function:

The test employed was that described in FR-2,734,825.

The melanin synthesis was estimated by incorporation of thiouracil. The specific melanogenesis activity was estimated by the ratio of the incorporation of "C thiouracil" to the incorporation of 3H leucine relative to 100% of the control (without retinoid).

Thus, the pigmenting activity was classified in the following manner:

Class 1: less than 30% specific melanogenesis activity,
Class 2: from 30% to 60% of specific melanogenesis activity,
Class 3: more than 60% of specific melanogenesis activity.

The $AC_{50}$ is the concentration for which 50% stimulation of melanogenesis relative to the control was observed.

The results are reported in the Table below:

TABLE

| Compound of formula | Pigmenting activity | $AC_{50}$ |
|---|---|---|
| (3) | Class 2 | $10^{-8}$ |
| (11) | Class 2 | $10^{-8}$–$10^{-7}$ |
| (17) | Class 1 | $<10^{-10}$ |
| (18) | Class 3 | ND |
| (13) | Class 3 | ND |
| (16) | Class 1 | ND |

ND: Not determined

By way of comparison, all-trans-retinoic acid, under the same conditions, had a pigmenting activity of Class 1, i.e., it had a depigmenting activity of Class 1 (less than 30% specific activity of melanogenesis inhibition).

FORMULATION EXAMPLES 2 to 19:

(1) ORAL ROUTE:

(a) The following composition was formulated as an 0.8 g tablet:

| | |
|---|---|
| Compound of formula (2) | 0.005 g |
| Pregelatinized starch | 0.265 g |
| Microcrystalline cellulose | 0.300 g |
| Lactose | 0.200 g |
| Magnesium stearate | 0.030 g |

For the treatment of a post-inflammatory hypopigmentation, 1 to 3 tablets were administered to an adult individual per day for 3 to 6 months depending on the severity of the case treated.

(b) The following drinkable suspension suitable for packaging in 5 ml vials was formulated:

| | |
|---|---|
| Compound of formula (4) | 0.050 g |
| Glycerol | 0.500 g |
| 70% Sorbitol | 0.500 g |
| Sodium saccharinate | 0.010 g |
| Methyl para-hydroxybenzoate | 0.040 g |
| Flavoring qs | |
| Purified water qs | 5 ml |

For the treatment of a hypopigmentation after a skin graft, 1 vial was administered to an adult individual per day for 3 months depending on the severity of the case treated.

(c) The following composition suitable for packaging in gelatin capsules was formulated:

| | |
|---|---|
| Compound of formula (5) | 0.025 g |
| Corn starch | 0.060 g |
| Lactose qs | 0.300 g |

The gelatin capsules comprised gelatin, titanium dioxide and a preservative.

For the treatment of vitiligo, 1 gelatin capsule was administered to an adult individual per day for 30 days.

(2) TOPICAL ROUTE:

(a) The following nonionic water-in-oil cream was formulated:

| | |
|---|---|
| Compound of formula (8) | 0.100 g |
| Mixture of emulsifying lanolin alcohols, waxes and refined oils, marketed by BDF under the trademark "anhydrous Eucerin" | 39.900 g |
| Methyl para-hydroxybenzoate | 0.075 g |
| Propyl para-hydroxybenzoate | 0.075 g |
| Sterile demineralized water qs | 100.000 g |

This cream was applied to a hypopigmented grafted skin once or twice a day for 30 days.

(b) A gel was formulated from the following composition:

| | |
|---|---|
| Compound of formula (11) | 0.050 g |
| Erythromycin base | 4.000 g |
| Butylhydroxytoluene | 0.050 g |
| Hydroxypropylcellulose, marketed by Hercules under the trademark "Klucel HF" | 2.000 g |
| Ethanol (950) qs | 100.000 g |

This gel was applied to a hypopigmented grafted skin 1 to 3 times a day for 6 to 12 weeks depending on the severity of the case treated.

(c) A lotion was formulated for correcting post-inflammatory hypopigmentation, by mixing together the following ingredients:

| | |
|---|---|
| Compound of formula (2) | 0.030 g |
| Propylene glycol | 5.000 g |
| Butylhydroxytoluene | 0.100 g |
| Ethanol (950) qs | 100.000 g |

This lotion was applied twice a day and a significant improvement was observed within a period of 2 to 6 weeks.

(d) A cosmetic sunscreen composition to combat the deleterious effects of sunlight was formulated by mixing together the following ingredients:

| | |
|---|---|
| Compound of formula (4) | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preservatives | 0.300 g |
| Propylene glycol | 2.000 g |
| Triethanolamine | 0.500 g |
| Fragrance | 0.400 g |

-continued

| | |
|---|---|
| Demineralized water qs | 100.000 g |

This composition was applied daily and combated light-induced aging.

(e) The following nonionic oil-in-water cream was formulated:

| | |
|---|---|
| Compound of formula (3) | 0.500 g |
| Vitamin D3 | 0.020 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100.000 g |

This cream was applied to a skin affected with vitiligo once or twice a day for 30 days.

(f) A topical gel was formulated by mixing together the following ingredients:

| | |
|---|---|
| Compound of formula (17) | 0.050 g |
| Ethanol | 43.000 g |
| α-Tocopherol | 0.050 g |
| Carboxyvinyl polymer marketed under the trademark "Carbopol 941" by Goodrich | 0.500 g |
| Triethanolamine as a 20% by weight aqueous solution | 3.800 g |
| Water | 9.300 g |
| Propylene glycol qs | 100.000 g |

This gel was applied to a skin affected with vitiligo 1 to 3 times a day for 6 to 12 weeks depending on the severity of the case treated.

(g) A hair lotion for repigmenting the hair was formulated by mixing together the following ingredients:

| | |
|---|---|
| Compound of formula (9) | 0.05 g |
| Compound marketed under the trademark "Minoxidil" | 1.00 g |
| Propylene glycol | 20.00 g |
| Ethanol | 34.92 g |
| Polyethylene glycol (molecular weight = 400) | 40.00 g |
| Butylhydroxyanisole | 0.01 g |
| Butylhydroxytoluene | 0.02 g |
| Water qs | 100.00 g |

This lotion was applied twice a day for 3 months to a scalp which had suffered considerable depigmentation.

(h) A post-cicatrization cream was formulated by mixing together the following ingredients:

| | |
|---|---|
| Compound of formula (13) | 0.050 g |
| Retinoic acid | 0.010 g |
| Mixture of glyceryl stearate and polyethylene glycol stearate (75 mol) marketed under the trademark "Gelot 6411 by Gattefosse | 15.000 g |
| Kernel oil polyoxyethylenated with 6 mol of ethylene oxide, marketed under the trademark "Labrafil M2130 CS" by Gattefosse | 8.000 g |
| Perhydrosqualene | 10.000 g |

-continued

| | |
|---|---|
| Preservatives qs | qs |
| Polyethylene glycol (molecular weight = 400) | 8.000 g |
| Disodium salt of ethylenediaminetetra-acetic acid | 0.050 g |
| Purified water qs | 100.000 g |

This cream was applied 1 to 3 times a day for 6 to 12 weeks.

(i) An oil-in-water cream was formulated from the following formulation:

| | |
|---|---|
| Compound of formula (4) | 0.020 g |
| Betamethasone 17-valerate | 0.050 g |
| S-carboxymethylcysteine | 3.000 g |
| Polyoxyethylene stearate (40 mol of ethylene oxide) marketed under the trademark "Myrj 5211 by Atlas | 4.000 g |
| Sorbitan monolaurate, polyoxyethylenated with 20 mol of ethylene oxide, marketed under the trademark "Tween 2011 by Atlas | 1.800 g |
| Mixture of glyceryl mono- and distearate marketed under the trademark "Geleol" by Gattefosse | 4.200 g |
| Propylene glycol | 10.000 9 |
| Butylhydroxyanisole | 0.010 g |
| Butylhydroxytoluene | 0.020 g |
| Cetostearyl alcohol | 6.200 g |
| Preservatives | qs |
| Perhydrosqualene | 18.000 g |
| Mixture of caprylic/capric triglycerides marketed under the trademark "Miglyol 81211 by Dynamit Nobel | 4.000 g |
| Triethanolamine (990i by weight) | 2.500 g |
| Water qs | 100.000 g |

This cream was applied twice a day to a skin affected with pigmentation problems due to aging.

(j) The following cream of oil-in-water type was formulated:

| | |
|---|---|
| Lactic acid | 5.000 g |
| Compound of formula (13) | 0.020 g |
| Polyoxyethylene stearate (40 mol of ethylene oxide) marketed under the trademark "Myrj 5211 by Atlas | 4.000 g |
| Sorbitan monolaurate, polyoxy-ethylenated with 20 mol of ethylene oxide, marketed under the trademark "Tween 2011 by Atlas | 1.800 g |
| Mixture of glyceryl mono- and distearate marketed under the trademark "Celeol" by Gattefosse | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preservatives | qs |
| Perhydrosqualene | 18.000 g |
| Mixture of caprylic/capric triglycerides marketed under the name "Miglyol 81211 Dynamit Nobel | 4.000 g |
| Water qs | 100.000 g |

(k) Dermal lotion for spraying:

| | |
|---|---|
| Compound of formula (15) | 5.000 g |
| Ethanol | 30.000 g |
| Demineralized water qs | 100.000 g |

(1) Hair lotion:

| | |
|---|---|
| Compound of formula (18) | 3.000 g |
| Propylene glycol | 30.000 g |
| Ethyl alcohol | 40.500 g |
| Water qs | 100.000 g |

This lotion was applied to the scalp once or twice a day at a rate of 1 ml per application.

(m) Thickened lotion:

| | |
|---|---|
| Compound of formula (1) | 5.000 g |
| Kawaine | 2.000 g |
| Hydroxypropylcellulose (Klucel G marketed by Hercules) | 3.500 g |
| Ethyl alcohol qs | 100.000 g |

This thickened lotion was applied to the scalp once or twice a day at a rate of 1 ml per application.

(n) Niosomal lotion:

| | |
|---|---|
| Chimexane NLO | 0.475 g |
| Cholesterol | 0.475 g |
| Monosodium stearoylglutamate | 0.050 g |
| Compound of formula (3) | 0.100 g |
| Preservatives qs | |
| Dyes qs | |
| Fragrance qs | |
| Demine-ralized water qs | 100.000 g |

This lotion was applied to the scalp once or twice a day at a rate of 1 ml per application.

(o) Lotion:

| | |
|---|---|
| Compound of formula (17) | 5.000 g |
| Propylene glycol monomethyl ether (Dowanol PM marketed by Dow Chemical) | 20.000 g |
| Hydroxypropylcellulose (Klucel G marketed by Hercules) | 3.000 g |
| Ethyl alcohol | 40.000 g |
| Minoxidil | 2.000 g |
| Water qs | 100.000 g |

This thickened lotion was applied to the scalp once or twice a day at a rate of 1 ml per application.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Method for promoting pigmentation of the skin and/or exoskeleton of an individual in need of such treatment, comprising administering to said individual an effective pigmentation-promoting amount of at least one retinoid compound which comprises a phenolic or naphtholic functional group.

2. The method as defined by claim 1, said individual being afflicted with, and treated for, vitiligo.

3. The method as defined by claim 1, said individual being afflicted with, and treated for, albinism.

4. The method as defined by claim 1, said individual being afflicted with, and treated for, post-inflammatory hypopigmentation.

5. The method as defined by claim 1, said individual being afflicted with, and treated for, post-inflammatory hypopigmentation/depigmantation consequent to skin grafting.

6. The method as defined by claim 1, said individual being afflicted with, and treated for, post-inflammatory hypopigmentation/depigmentation consequent to ultraviolet irradiation.

7. The method as defined by claim 1, said individual being afflicted with, and treated for, post-inflammatory hypopigmentation/depigmentation consequent to post-cicatrization.

8. The method as defined by claim 1, said individual being afflicted with, and treated for, post-inflammatory hypopigmentation/depigmentation consequent to aging or lentigo.

9. The method as defined by claim 1, said individual being afflicted with, and treated for, objectionable nail pigmentation.

10. The method as defined by claim 1, said individual being afflicted with, and treated for, objectionable hair coloration.

11. The method as defined by claim 1, said at least one retinoid compound being formulated into cosmetically/pharmaceutically acceptable carrier, diluent or vehicle therefor.

12. The method as defined by claim 1, comprising topically applying said at least one retinoid compound onto the skin, hair, and/or nails of said individual.

13. The method as defined by claim 1, comprising orally or systemically administering said at least one retinoid compound to said individual.

14. The method as defined by claim 1, said at least one retinoid compound comprises 6-[3-(1-adamantyl)-4-methoxyphenyl]-2-naphthoic acid; methyl 6-[3-(1-adamantyl)-4-hydroxyphenyl]-2-naphthoate; 6-[3-(1-adamantyl)-4-hydroxyphenyl]-2-naphthoic acid; 6-[3-(I-adamantyl)-4-acetoxyphenyl]-2-naphthoic acid; [3-[3-(1-adamantyl)-4-methoxyphenyl]-2H-1-benzopyran]-7-carboxylic acid; [3-[3-(1-adamantyl)-4-hydroxyphenyl]-2H-1-benzopyran]-7-carboxylic acid; [3-[3-(1-adamantyl)-4-acetoxyphenyl]-2H-1-benzopyran]-7-carboxylic acid; [2-[3-(1-adamantyl)-4-hydroxyphenyl]benzimidazole]-5-carboxylic acid; [2-[3-(1-adamantyl)-4-hydroxyphenyl]benzothiophene-6-carboxylic acid; [2-[3-(1-adamantyl)-4-hydroxyphenyl]benzofuran-6-carboxylic acid; 4-[(E)-2-[3-(1-adamantyl)-4-hydroxyphenyl]propenyl]benzoic acid; 4-[2-[3-(1-adamantyl)-4-hydroxyphenyl]ethynyl]benzoic acid; 3-[(3,5-di-tert-butyl-4-hydroxyphenyl)-2H-1-benzopyran]-7-carboxylic acid; methyl 3-[(3,5-di-tert-butyl-4-hydroxyphenyl)-2H-1-benzopyran]-7-carboxylate; 6-[2-[3-tert-butyl-4-hydroxyphenyl]naphthoic acid; 4-[(E)-2-[3,5-di-tert-butyl-4-hydroxyphenyl]ethenyl]benzoic acid; 4-[(E)-2-[3,5-di-tert-butyl-4hydroxyphenyl]propenyl]-benzoic acid; 4-[3-(3,5-di-tert-butyl-4-hydroxyphenyl)-1-propynyl]benzoic acid; (all-E)-9-(3-(1-adamantyl)-4-hydroxyphenyl)-3,7-dimethyl-2,4,6-nonatrienoic acid; (all-E)-9-(4-hydroxy-2,3,6-trimethylphenyl)-3,7-dimethyl-2,4,6,8-nonatetraenoic acid; ethyl (all-E)-9-(4-methoxy-2,3,6-trimethylphenyl)-3,7-dimethyl-2,4,6,8-nonatetraenoate; 4-[6-hydroxy-7-(1-adamantyl)-2-naphthyl]benzoic acid; or 4-[(E)-2-[3-tert-butyl-4-hydroxyphenyl)propenyl]benzoic acid.

15. The method as defined by claim 1, comprising co-administering to said individual an effective amount of at least one enzyme exhibiting tyrosinase activity.

16. The method as defined by claim 15, said at least one enzyme exhibiting tyrosinase activity comprising tyrosine or derivative thereof, 3,4-dihydroxyphenyl-α-alanine, or 5,6-dihydroxyindole.

17. The method as defined by claim 15, comprising simultaneously or separately administering and co-administering said at least one retinoid compound and said at least one enzyme exhibiting tyrosinase activity.

18. A cosmetic/pharmaceutical composition of matter suited for promoting pigmentation of the skin and/or exoskeleton of an individual in need of such treatment, comprising (a) an effective pigmentation-promoting amount of at least one retinoid compound which comprises a phenolic or naphtholic functional group, and (b) an effective amount of at least one enzyme exhibiting tyrosinase activity.

19. The cosmetic/pharmaceutical composition as defined by claim 18, said at least one enzyme (b) exhibiting tyrosinase activity comprising tyrosine or derivative thereof; 3,4-dihydroxyphenyl-α-alanine or 5,6-dihydroxyindole.

20. A cosmetic/pharmaceutical composition of matter suited for promoting pigmentation of the skin and/or exoskeleton of an individual in need of such treatment, comprising (a) an effective pigmentation-promoting amount of at least one retinoid compound which comprises a phenolic or naphtholic functional group, and (b) an effective amount of at least one antibacterial agent, antiparasitic agent, antifungal agent, antiviral agent, anti-inflammatory agent, antipruriginous agent, anaesthetic, keratolytic agent, anti-free-radical agent, anti-seborrhoeic agent, antidandruff agent, antiacne agent and/or an agent which reduces skin differentiation and/or proliferation and/or pigmentation, or an extract of plant or bacterial origin.

21. The methodology as defined by claim 1, said at least one retinoid compound being formuated into tablets, gelatin capsules, sugar-coated tablets, a syrup, a suspension, a solution, a powder, granules, an emulsion, microspheres or nanospheres, lipid or polymer vesicles permitting controlled release, a lotion, a serum, a dispersion, a cream, a gel, a mousse, a shampoo, a soap, or an aerosol.

22. The methodology as defined by claim 1, comprising administering to said individual in need of such treatment, per diem, from 0.01 mg/kg to 100 mg/kg of said at least one retinoid compound.

23. A kit comprising a plurality of separate compartments, at least one first compartment confining an effective pigmentation-promoting amount of at least one retinoid compound which comprises a phenolic or naphtholic functional group and at least one second compartment confining an effective amount of at least one enzyme exhibiting tyrosinase activity.

* * * * *